(12) United States Patent
Han et al.

(10) Patent No.: US 6,270,814 B1
(45) Date of Patent: Aug. 7, 2001

(54) INCORPORATION OF WHEY INTO PROCESS CHEESE

(75) Inventors: Xiao-Qing Han, Naperville, IL (US); Joseph E. Spradlin, Hot Springs, AR (US)

(73) Assignee: Kraft Foods, Inc., Northfield, IL (US)

( * ) Notice: Subject to any disclaimer, the term of this patent is extended or adjusted under 35 U.S.C. 154(b) by 0 days.

(21) Appl. No.: 09/325,220

(22) Filed: Jun. 3, 1999

(51) Int. Cl.$^7$ ........................................ A23C 9/12
(52) U.S. Cl. ........................ 426/36; 426/34; 426/38; 426/40; 426/583
(58) Field of Search ........................ 426/34, 36, 580, 426/583, 38, 40, 42

(56) References Cited

U.S. PATENT DOCUMENTS

| | | |
|---|---|---|
| 3,535,304 | 10/1970 | Muller et al. . |
| 4,205,090 | 5/1980 | Maubois et al. . |
| 5,156,956 | 10/1992 | Motoki et al. . |
| 5,356,639 | 10/1994 | Jameson et al. . |
| 5,523,237 | 6/1996 | Budtz et al. . |
| 5,681,598 | 10/1997 | Kuraishi et al. . |
| 5,731,183 | 3/1998 | Kobayashi et al. . |

FOREIGN PATENT DOCUMENTS

| | | |
|---|---|---|
| 59-059151 | 4/1984 | (JP) . |
| 02276541 | 11/1990 | (JP) . |
| 93/22930 | 11/1993 | (WO) . |
| 94/21129 | 9/1994 | (WO) . |
| 94/21130 | 9/1994 | (WO) . |
| 97/01961 | 1/1997 | (WO) . |

OTHER PUBLICATIONS

Ernstrom et al., J. Dairy Science 63:2298–234 (1980).

Banks, J.M. et al., IG [1987]. Increasing the yield of Cheddar Cheese by the acidification of milk containing heat–denatured whey protein. Milchwissenschft 42 (4), pp. 212–215.

Law, A.J.R. et al., IG [1994]. Denaturation of the whey proteins in heat milk and their incorporation into Cheddar cheese. Milchwissenschaft 49 (2), pp. 63–67.

Guinee, Timothy P. et al., Composition, Microstructure and Maturation of Semi–Hard Cheeses From High Protein Ultra-filtered Milk Retentates With Different Levels of Denatured Whey Protein, Int. Dairy Journal 5, p. 543–568.

Han, Xiao–Qing et al., [1996]. Thermodynamic Compatibility of Substrate Proteins Affects Their Cross–Linking by Transglutaminase. J. Agri. Food Chem. 44 (5) pp. 1211–1217.

Dybing S. T., et al. [1998], Dairy Foods—The Ability of Phosphates or—Carrageenan to Coagulate Whey Proteins and the Possible Uses of Such Coagula in Cheese Manufacture. J. Dairy Sci. 81 (2) pp. 309–317.

Dalgleish, D. G., et al., [1997] Heat–Induced Interactions of Whey Proteins and Casein Micelles with Different Concentrations of $\alpha$–Lactalbumin and $\beta$–Lactoglobulin, J. Agric. Food. Chem., 45, pp. 4806–4813.

Dalgleish, D. G., et al. [1997] Interactions between $\alpha$–Lactalbumin and $\beta$–Lactoglobulin in the Early Stages of Heat Denaturation, J. Agric Food Chem. 45 pp. 3459–3464.

Noh, B., et al. [1989] Incorporation of Radiolabeled Whey Proteins into Casein Micelles by Heat Processing, J. Dairy Sci. 72 pp. 1724–1731.

Noh, B., et al. [1989] Radiolabelling Study of Heat–induced Interactions Between $\alpha$–Lactalbumin, $\beta$–Lactoglobulin and $\kappa$–Casein in Milk and in Butter Solutions, Journal of Food Science, vol. 54, No. 4, pp. 889–893.

*Primary Examiner*—Leslie Wong
(74) *Attorney, Agent, or Firm*—Fitch, Even, Tabin & Flannery

(57) ABSTRACT

The present invention provides a process cheese product made with a cheese and dairy liquid that includes casein, whey protein, and lactose, wherein at least a portion of the casein and/or whey protein in the dairy liquid is crosslinked via $\gamma$-carboxyl-$\epsilon$-amino crosslinks prior to being combined with the cheese, and wherein the lactose in the process cheese product remains dissolved in the aqueous phase upon storage. According to the invention, this product is provided by a process that includes the important step of contacting the dairy liquid with a transglutaminase for a time, and under conditions, sufficient to crosslink at least a portion of the casein and/or whey protein to provide crosslinked protein conjugates in the dairy liquid. The invention furthermore provides the process for making the process cheese product. Advantageously, the process permits replacing part of the cheese proteins with the crosslinked proteins of the dairy liquid. Additionally, crystallization of lactose in the process cheese product is significantly inhibited such that lactose levels higher than commonly introduced in cheese products may be employed in the process cheese of the invention.

21 Claims, 1 Drawing Sheet

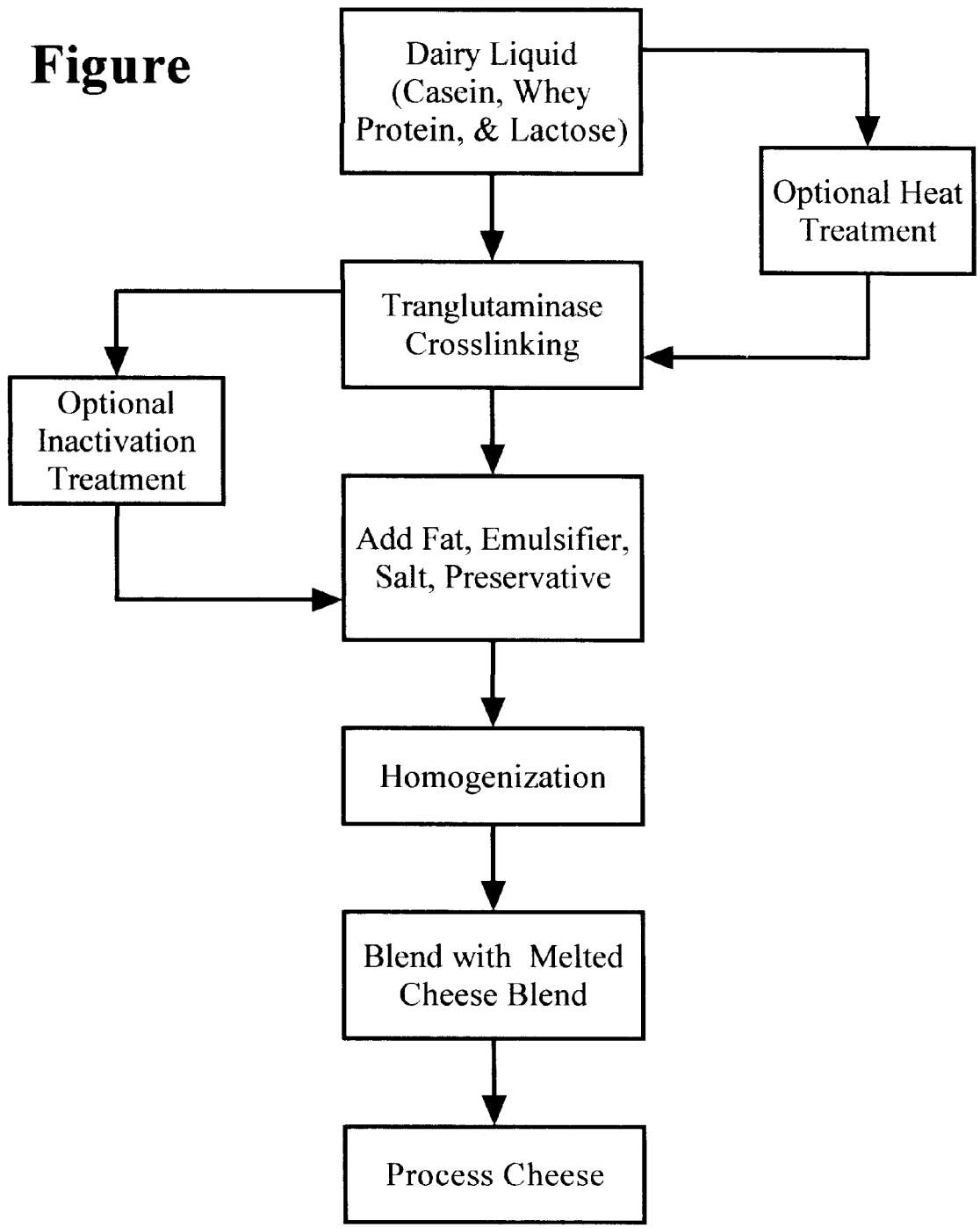
Figure

INCORPORATION OF WHEY INTO PROCESS CHEESE

FIELD OF THE INVENTION

This invention relates to a method that increases the incorporation of whey proteins and lactose into process cheese. The method applies transglutaminase crosslinking of whey and milk proteins prior to blending with cheese to provide a process cheese. The resulting process cheese includes a significant proportion of whey protein and supersaturated lactose in the moisture phase.

BACKGROUND OF THE INVENTION

Cheese compositions are generally prepared from dairy liquids by processes that include treating the liquid with a coagulating or clotting agent. The coagulating agent may be a curding enzyme, an acid, or a suitable bacterial culture or it may include such a culture. The coagulum or curd that results generally incorporates transformed casein, fats including natural butter fat, and flavorings that arise especially when a bacterial culture is used. The curd is usually separated from the whey. The resulting liquid whey generally contains soluble proteins not affected by the coagulation; such proteins are, of course, not incorporated into the coagulum. Whey also includes low molecular weight components, such as lactose and salts. The inability of whey proteins to be retained in the coagulum is an important factor contributing to a lack of efficiency in production of cheese curds, and to a reduction in overall yield relating to the incorporation of all the protein solids that are present in the starting dairy liquids into resulting cheese curds. Furthermore, lactose is incorporated with difficulty into cheese products because, under the conditions prevalent in cheese during storage, lactose crystallizes from the aqueous phase, thereby producing a graininess that detracts from the overall organoleptic quality of the cheese product. Nevertheless, increased incorporation of lactose into cheese products would increase the efficiency of use of all the nutritive components present in the starting dairy liquids. These problems have been recognized for many years.

Several methods were proposed early with the objective of recovering whey proteins in cheese products. For example, whey proteins have been concentrated or dried from whey, and then recombined with cheese (see, e.g., Kosikowski, Cheese and Fermented Foods, 2nd ed., Edwards Brothers, Inc., Ann Arbor, Mich., 1977, pp. 451–458). Unfortunately the whey recovered from such procedures does not have the appropriate physical and chemical properties conducive to making good quality natural cheeses or process cheeses. An alternative approach has been to coprecipitate whey proteins with casein, as disclosed, for example, in U.S. Pat. No. 3,535,304. Again, however, the final product of this process lacks the proper attributes for making processed and imitation cheeses.

A further attempt to incorporate whey proteins into cheese products has employed ultrafiltration of milk to concentrate the components, such as casein, whey protein, and butterfat, that do not permeate the ultrafiltration membrane. When such a composition is coagulated by contact with an acid or rennet, a curd forms. This curd, however, loses considerable quantities of the whey protein during compaction. An example of such a process is provided in U.S. Pat. No. 4,205,090 wherein the milk is concentrated to about one-fifth of its original volume. The resulting curd could only be used to provide soft cheeses such as Camembert or Roblechon. Hard cheeses, such as cheddar, Colby, and the like, could not be prepared using this method.

Ernstrom et al. (J. Dairy Science 63:2298–234 (1980)) described a process in which milk is concentrated to about 20% of the original volume by ultrafiltration, diafiltration, and evaporation. The resulting composition is then inoculated with a cheese starter to ferment the lactose and form a cheese base. The cheese base can be used to replace natural cheese components of process cheese. This process does not employ any renneting step to prepare a cheese curd.

Food processing methods employing transglutaminases have also been disclosed in recent years. For example, Japanese Patent 59059151 discloses treating an emulsion containing proteins, oils or fats, and water with transglutaminase to produce a gelatinous, crosslinked gel. Japanese Patent 02276541 discloses a heat-resistant food protein having a fiber texture. The fiberlexture is developed by treatment of a protein hydrogel with a transglutaminase in the presence of calcium ion to induce crosslinking of the surface of a fiber bundle.

U.S. Pat. No. 5,156,956 discloses a transglutaminase purified from strains of the genus Streptoverticillium, as well as its chemical, physical, and enzymatic properties. This transglutaminase catalyzes formation of protein gelation products from protein solutions to produce conventional gel foodstuffs such as yoghurt, jelly, cheese, gel cosmetics, and the like. This method did not use transglutaminase and enzymatic clotting agents to produce cheese.

U.S. Pat. No. 5,356,639 discloses a process for the production of a fermented concentrate from milk, including whole milk, skim milk, and milk with added milk components. The concentrate could be used to make cheese. The process includes the steps of (1) selectively concentrating milk; (2) increasing the ionic strength of the concentrate to maintain the milk in the liquid phase (coagulum formation is prevented both during and after fermentation); (3) fermenting the concentrate with lactic acid producing bacteria; and (4) removing water from the fermented liquid concentrate. The final product includes substantially all of the whey proteins originally present in the milk.

U.S. Pat. No. 5,681,598 describes a process for producing cheese with a transglutaminase. The process includes (1) adding a transglutaminase to a milk or milk protein solution, (2) heat-treating the mixture, (3) adding a milk clotting enzyme for a fixed time, and (4) recovering a cheese. This process provides a large amount of cheese curd compared to conventional methods. Additionally, processes in which conventional cheese fermentation occurs first and transglutaminase treatment occurs subsequently, as well as simultaneous treatments, are disclosed. The milk clotting enzyme is preferably an animal rennet. Increases in total weight, but not in dry weight, of the curd when using transglutaminase were observed.

U.S. Pat. No. 5,731,183 discloses a transglutaminase purified from strains of *Bacillus subtilis*, having particular physical and enzymatic characteristics, and a method for producing protein, peptide, or non-protein amino acid polymers that are crosslinked via their glutamine and lysine residues to form intermolecular or intramolecular conjugates. The transglutaminase may be used to produce crosslinked protein polymers that can be used in a variety of food substances, including cheese.

Banks et al. (*Milchwissenschaft* 42:212–215 (1987)) disclose that heating milk at temperatures from 95° C. to 140° C. and then acidifying permits a modest increase in protein content in the cheese upon Cheddar production. Unfortunately, the resulting cheese developed a bitter off-flavor. Law et al. (*Milchwissenschaft* 49:63–37 (1994))

report that heat treatment of milk prior to cheddaring results in reduction of proteins in whey and/or in acid filtrates of the milk.

Han et al. (*J. Agri. Food Chem.* 44:1211–1217 (1996)) examined the activity of transglutaminase in forming heterologous dimers and trimers. It was found that β-casein forms homopolymers whereas β-lactoglobulin does not. In heterologous mixtures, transglutaminase was shown to catalyze dimer formation between α-lactalbumin and β-casein but not between β-casein and β-lactoglobulin. Cheese production is not discussed.

U.S. Pat. No. 5,523,237 discloses a plastein material which is defined as one made by reversing the activity of a protease enzyme (e.g., a serine protease) acting on proteinaceous material. The proteinaceous substrate is present at a concentration of 5–50%, and is preferably whey, casein, or soy protein. The enzyme preparation is substantially free of subtilisin A activity, and is specific for glutamic acid and aspartic acid residues. This protease, designated SP 446, is obtained from *Bacillus licheniformis*. Its proteolytic activity is characterized in considerable detail. The viscosity of whey protein containing solutions is shown to increase as a result of the action of the enzyme.

International patent WO 93/22930 discloses treating milk with a transglutaminase (preferably mammalian activated Factor XIII) and then with an enzyme having milk clotting activity to provide a milk-like product. The product is reported to contain microparticulated protein that has been aggregated by means of the enzyme with milk clotting activity, and has mouthfeel that resembles a fat emulsion. Preferably the milk clotting enzyme is a cheese rennet enzyme. This method, like that of U.S. Pat. No. 5,356,639, does not appear to provide a cheese curd.

International patent WO 94/21129 discloses a process for forming an acidified edible gel from milk. Transglutaminase is added to milk or a milk-like product, the pH is adjusted to 4.8 to 5.8, and the resulting composition is exposed to a heat treatment. The resulting edible gel is reported to have a pleasant consistency and mouthfeel. International patent WO 94/21130 discloses a similar process for forming an edible gel from milk. Transglutaminase is added to milk or a milk-like product, rennet is then added, and the resulting composition is exposed to a heat treatment. It is stated that a surprising result is the lack of separation of a curd and a whey phase as is normal upon rennet treatment. The product is a single phase gel which is reported to have satisfactory organoleptic properties.

International patent WO 97/01961 discloses a process for making cheese which retains proteins in the cheese. The milk is incubated with transglutaminase, followed by a treatment with a rennet to cause clotting and formation of a coagulate. After separating the whey from the coagulate, the coagulate is used to make cheese. The protein to be maintained in the cheese, as set forth in the description, relates to casein macropeptides that result from the action of the rennet, and that diffuse into the whey. This process differs from the instantly claimed invention in a number of ways. The process disclosed in this patent relates to the retention of casein macropeptides, rather than whey protein, in the cheese curd. Moreover, there is no requirement for an initial heating step, and the rennet employed in WO 97/01961 is a conventional mammalian rennet.

Dybing et al. (*J. Dairy Sci.* 81:309–317 (1998)) postulated incorporating whey protein into cheese curd by concentrating the components, coagulating whey proteins using a variety of agents, and renneting a composition containing the coagulated whey protein and concentrated milk components. It was found, however, that none of the attempted methods succeeded in producing whey protein coagula that could be recovered as cheese.

Guinee et al. (*Int. Dairy Journal* 5:543–568 (1995)) reviewed the state of the art relating to incorporation of whey protein into cheese. High-heat treatment of milk impairs rennet coagulation, curd syneresis, curd structure and texture, as well as functional properties such as meltability and stretchability. Guinee et al. discuss physical and chemical factors that may be responsible for these effects. In heat treatments that denature whey protein in milk compositions, they found that, in semi-hard cheeses that result from curding such treated compositions, the curd has higher whey protein levels, but also higher moisture level, lower pH value, poorer curd fusion and lower yield (fracture) values during ripening.

Heat treatment of whey proteins, either alone (Dalgleish et al., J. Agric. Food Chem. 45:3459–3464 (1997)), or in the presence of milk proteins, i.e., caseins (Noh et al., J. Dairy Sci. 72:1724–1731 (1989); Noh et al., J. Food Sci. 54:889–893 (1989); Dalgleish et al., J. Agric. Food Chem. 45:4806–4813 (1997)), has been shown to lead to aggregation and crosslinking of α-lactalbumin and β-lactoglobulin; in the presence of milk the crosslinking involves κ-casein. Significantly, this process involves the formation of intermolecular disulfide linkages between the component proteins.

In spite of many attempts documented over almost three decades of effort, there remains a need for a process cheese that incorporates a significant amount of casein and whey proteins without sacrificing cheese flavor, cheese texture, and overall favorable organoleptic properties, and for a process of preparing a process cheese incorporating a significant amount of casein and whey proteins that retains cheese flavor, cheese texture and favorable organoleptic properties. There additionally remains a need for a process cheese incorporating a large amount of lactose without resulting in crystallization of lactose, and for a process that significantly increases the amount of lactose that may be incorporated into process cheese without crystallizing the lactose. Additionally there remains a need for enhancing the yield and efficiency of making process cheese that relates to optimizing the incorporation of casein, whey protein, and lactose into process cheese products without developing graininess or grittiness due to crystallization of excess lactose. The present invention discloses methods and process cheese compositions that address these needs.

SUMMARY OF THE INVENTION

The present invention provides a cheese and dairy liquid wherein the dairy liquid contains casein, whey protein, and lactose, wherein at least a portion of the casein or whey protein in the dairy liquid has been crosslinked via γ-carboxyl-ε-amino crosslinks whose formation is catalyzed using transglutaminase, prior to being combined with the cheese, and wherein the lactose in the process cheese product remains dissolved upon storage at refrigerated temperature. According to the invention, this product is provided by a process that includes the sequential steps of (i) preparing a dairy liquid comprising casein, whey protein, and lactose;

(ii) contacting the dairy liquid with a transglutaminase for a time, and under conditions, sufficient to crosslink at least a portion of the casein and/or whey protein to provide a crosslinked dairy liquid;

(iii) combining the crosslinked dairy liquid with one or more compositions wherein the compositions, taken together, include a fat, an emulsifier, a salt, and a preservative, and homogenizing the combination;

(iv) adding the homogenized combination to a melted cheese to form the process cheese; and (v) heating the process cheese to a temperature of 170° F. to 200° F. for 1 min to 10 min, and then cooling and packaging.

In significant embodiments of the process cheese, the transglutaminase is isolated from a microbial source, a fungus, a mold, a plant, a fish, or a mammal; in still more significant embodiments, the transglutaminase is isolated from a microbial source, preferably from the genus Streptoverticillium. In an additional important embodiment, the process providing the process cheese further includes heating the dairy liquid at a temperature between about 120° F. and about 200° F. for a time between about 2 minutes and about 100 minutes before treating with transglutaminase. In a further advantageous embodiment, the dairy liquid is contacted with transglutaminase at a temperature from about 50° F. to about 150° F. for a time between about 10 minutes and about 300 minutes; preferably, the temperature is about 75° F. and about 125° F. and the time is between about 30 minutes and about 60 minutes.

In yet an additional significant embodiment, the process cheese is provided by a process that further includes heating the crosslinked dairy liquid at a temperature and for a time sufficient to inactivate the transglutaminase after the enzyme treatment and before adding the compositions of step (iii). In equally significant aspects, the invention provides the process for making the process cheese product described in the preceding paragraphs.

BRIEF DESCRIPTION OF THE DRAWING

The FIGURE is a flow chart illustrating the invention, including several optional treatment steps.

DETAILED DESCRIPTION OF THE INVENTION

The method of this invention is illustrate in the FIGURE. The starting material of the present invention is a dairy liquid that includes casein and whey, including whey proteins and lactose. As used herein, "dairy liquid" relates to milk, milk products obtained by fractionating raw milk to provide a liquid fraction, or a solid milk fraction that is reconstituted to a liquid. For example, the milk may be treated to remove some or all of the butterfat, providing low fat milk or skim milk, respectively. Furthermore, whole milk, low fat milk, or skim milk may be concentrated by methods such as evaporation and/or ultrafiltration (with or without diafiltration) and the like. Evaporation provides dairy liquids containing a higher concentration of all the nonvolatile components, whereas ultrafiltration provides dairy liquids with a higher concentration of the components that do not permeate the ultrafiltration membrane. In any case, the dairy proteins including casein and whey protein are included among the retained solids, such that their concentrations in the resulting liquids are increased. Furthermore any of the above dairy liquids may be evaporated to dryness, providing milk solids originating from whole milk, low fat milk, or skim milk, and including casein, whey proteins, and lactose. Any of these solids may be reconstituted by the addition of water or a suitable aqueous composition including milk or a milk fraction. Reconstitution of dry milk thus provides dairy liquids that in general may have a broad range of final concentrations of the component proteins, lactose, butterfat, and other components. All the above liquids are included in the designation of "dairy liquids" as used herein.

The dairy liquids employed in the present invention may originate from any lactating livestock animal whose milk is useful as a source of human food. Such livestock animals include, by way of nonlimiting example, cows, buffalo, other ruminants, goats, sheep, and the like. Generally, however, cows' milk is the preferred dairy liquid used in the practice of the invention.

As used herein, "casein" relates to any, or all, of the phosphoproteins in milk, and to mixtures of any of them. An important characteristic of casein is that it forms micelles in naturally occurring milk and in the dairy liquids employed in the present invention. Many casein components have been identified, including, but not limited to, $\alpha$-casein (including $\alpha_{s1}$ casein and $\alpha_{s2}$ casein), $\beta$-casein, $\kappa$-casein, and their genetic variants.

As used herein, "whey protein" relates to the proteins contained in the dairy liquid (i.e., whey) obtained as a supernatant of the curds when milk or a dairy liquid containing milk components are curded to produce a cheese-making curd as a semisolid. Whey protein is generally understood to include principally the globular proteins $\beta$-lactoglobulin and $\alpha$-lactalbumin. It may also include significantly lower concentrations of immunoglobulin and other globulins.

Transglutaminases are enzymes which catalyze the transfer of the $\gamma$-carboxamide group of a glutaminyl residue in a protein or peptide to the $\epsilon$-amino of a lysyl residue of the same or a different protein or peptide, thereby forming a $\gamma$-carboxyl-$\epsilon$-amino crosslink. Transglutaminases have a broad occurrence in living systems, and may be obtained, for example, from microorganisms such as those belonging to the genus Streptoverticillium, or from *Bacillus subtilis*, from various Actinomycetes and Myxomycetes, from fish species and other marine sources, from plant sources, and from animal sources, especially mammals. Mammals provide the blood clotting protein activated Factor XIII, and liver transglutaminase obtained, for example, from pigs. In general, transglutaminases from animal sources require calcium ions for activity. Recombinant forms of transglutaminase enzymes may be obtained by genetic engineering methods as heterologous proteins produced in bacterial, yeast, and insect or mammalian cell culture systems. The principal requirement of any transglutaminase employed in the instant invention is that it have the activity referred to above. Any enzyme having transglutaminase activity may be employed in the methods of the present invention. In a preferred embodiment, the transglutaminase is obtained from the genus Streptoverticillium.

Transglutaminase activity may be determined using known procedures. One such calorimetric procedure uses benzyloxycarbonyl-L-glutaminyl-glycine and hydroxylamine to form a $\gamma$-carboxyl-hydroxamic acid if transglutaminase is present. An iron complex of the hydroxamic acid can be formed in the presence of ferric chloride and trichloroacetic acid. Using the absorbance at 525 nm with appropriate standards, the activity of enzyme present may be determined. See, for example, U.S. Pat. No. 5,681,598.

In order to practice the method of the invention, and to prepare the process cheese of the invention, a dairy liquid containing casein, whey proteins, and lactose is prepared or obtained. This starting composition is such that, upon treatment according to the method presented herein, the proportion of melted cheese that is combined with the above ingredients to form the process cheese product is low, compared to the proportion employed in a conventional process cheese. In general, the amount of lactose used is such that its concentration in the aqueous phase corresponds to supersaturation under the conditions of storage of the process cheese product. The process of the invention succeeds in incorporating high levels of lactose into the process cheese product in a way that maintains the lactose solubilized, and does not lead to formation of significant amounts of lactose crystals during storage (e.g., at least three months at a temperature of about 50° F.).

In the process of the invention, the dairy liquid containing casein, whey proteins, and lactose is crosslinked at a temperature, and for a duration in time, that are sufficient to inhibit or prevent crystallization of the lactose after formation of the process cheese. In this regard, crystallization of lactose in the process cheese product differs considerably from the crystallization of lactose in a simple two-component single phase system such as an aqueous solution or syrup of lactose. In the process cheese product, the water activity is considerably lower than in an aqueous solution, the number of phases is greater than one (including interfaces between aqueous and immiscible nonaqueous phases), and the process cheese product may include emulsified microphases. All these distinctions may act to enhance the tendency for lactose to crystallize in conventional cheese products compared to that in an aqueous single phase system.

Without wishing to be limited by theory, it is believed that, in the present inventive method, the enzymatic crosslinking of the proteins leads to enhanced hydration of the proteins (i.e., effective dispersion, dissolution and solvation of the proteins of the dairy liquid). Additionally, an optional preliminary heating step prior to the cross-linking step appears to eliminate or significantly reduce lactose crystal seeds (i.e., all microcrystals), and to effect partial denaturation of the whey proteins in the dairy liquid. Thus, the present invention minimizes and/or prevents crystallization of lactose in the process cheese product upon storage.

The action of a transglutaminase on the dairy liquid is used to effect the desired crosslinking. Prior to treatment with the enzyme, however, the dairy liquid may optionally be heated at a temperature between about 120° F. and about 200° F. for a time between about 2 minutes and about 100 minutes. Since transglutaminase catalyzes crosslinking between the side chains of protein molecules, it is thought, although not wishing to be limited by theory, that partial denaturation of the protein molecules intended to be crosslinked may expose more potential crosslinking sites to the aqueous solvent. Those side chains would be more accessible to the transglutaminase, thereby increasing the amount of crosslinking. This heat treatment, when included in the process employed, is intended to bring about a partial denaturation of the protein molecules in order to accomplish the above stated objective.

In the treatment with transglutaminase, an amount of an enzyme preparation having sufficient transglutaminase activity to crosslink at least a portion of the casein and/or whey protein is added to the dairy liquid, and the treatment is allowed to continue for a time sufficient to accomplish the crosslinking under the particular conditions employed. As indicated above, the known enzymatic activity of transglutaminase is to catalyze the transfer of the γ-carboxamide group of a glutaminyl residue in a protein or peptide to the ε-amino of a lysyl residue of the same or a different protein or peptide. Without wishing to be bound by theory, if such reactions were to occur in the dairy liquid, glutaminyl-lysyl side chain-side chain crosslinks would form between the protein components present, including crosslinks among and between the caseins and the whey proteins. The treated dairy liquid produced by the action of the transglutaminase may include protein molecules crosslinked in this fashion. Generally, the treatment with transglutaminase is continued at a temperature of about 50° F. to about 150° F. for about 10 min to about 300 min, and preferably at a temperature of about 75° F. to about 125° F. for about 30 min to about 60 min.

After crosslinking the proteins of the dairy liquid with transglutaminase, the enzyme may optionally be inactivated by, for example, a brief exposure of the modified dairy liquid to an elevated temperature sufficient to achieve inactivation. Inactivation is not, however, required. When the transglutaminase is not deliberately inactivated by such a heat treatment, any transglutaminase activity that survives under the conditions used in the succeeding steps of the method is capable of catalyzing further crosslinking reactions. The heat treatment of the process cheese will likely inactivate any remaining activity.

The crosslinked dairy liquid resulting from the transglutaminase treatment is then combined with one or more compositions, wherein the compositions, taken together, include a fat, an emulsifier, a salt, and a preservative, and the resulting combination is homogenized. Commonly, the fat includes butter, and may include additional fatty or lipid components. The emulsifier is generally chosen from among sodium phosphate, monosodium phosphate, and disodium phosphate, and any mixture thereof, and the salt is chosen from among table salts. Commonly, the preservative is sorbic acid or an alkali salt thereof. Other known preservatives may also be used.

The homogenized combination is then added to a melted cheese to form process cheese. The melted cheese has been preheated; it may optionally have added to it flavorants and/or colorants in order to provide appealing characteristics to the final product. Generally, the temperature at which a cheese must be heated to melt it sufficiently to receive the dairy liquid combination is between about 150° F. and about 200° F. The resulting process cheese is thoroughly blended in the melted state. It is then pasteurized by heating it at a temperature of about 170° F. to 200° F. for 1 min to 10 min, and then cooling and packaging.

The process cheese product resulting from this process has several advantages over process cheeses known in the art. The protein polymers produced by the crosslinking with transglutaminase appear to behave in novel ways as being more hydrophilic than the component uncrosslinked proteins. The crosslinked proteins appear to have undergone changes to the functionality of the proteins; it is found that this altered functionality permits replacing part of the cheese proteins with the crosslinked proteins of the dairy liquid. Additionally, the crosslinked proteins appear to alter the water binding properties of the cheese system. As a result, crystallization of lactose in the process cheese product is significantly retarded; indeed, relatively high lactose contents may be employed in the process cheese of the invention without forming lactose crystals in the process cheese (even during prolonged storage). These factors combine to permit the manufacture of process cheese containing significant levels of whey protein and lactose, thus, increasing the efficiency of the process compared to conventional process cheese processes.

Additional advantageous attributes include improvement in the melting behavior of the final product, because transglutaminase crosslinked protein conjugates are more hydrophilic compared to the intact (i.e., uncrosslinked), protein. In addition, the heat treatment applied to promote the transglutaminase cross-linking reaction largely eliminates the possibility that contaminating microorganisms from added ingredients survive in the final product, hence increasing the stability of the product to microbiological contamination.

EXAMPLES

Example 1

Treatment of Dairy Liquid with Transglutaminase Prior to Addition to Melted Cheese An experimental composition incorporating the features of the invention was prepared, and was compared with a control composition representative of process cheeses currently being marketed. Their respective compositions are presented in Table 1.

To prepare the control sample, first dry whey (containing 71.78% lactose, the sole source of lactose; Krafen, Kraft Foods, Glenview Ill.), whey protein concentrate (WPC34, Wisconsin Whey International, Juda, Wis.) containing 34% whey protein) and milk protein concentrate (NZ MPC-70, New Zealand Milk Products, Wellington, New Zealand) were mixed with water to make a wet mix. Separately, a conventional cheese blend was blended with conventional colorants and heated to melting. Salt, acid, emulsifiers (MSP (monosodium phosphate) and DSP (disodium phosphate)), and melted butter were added to the melted cheese blend and mixed. Then the wet mix was added and mixed, and heated to 176° F. for 1 min, and the result was passed through a vacuum flash tank to eliminate air bubbles.

In order to prepare the inventive sample, milk protein concentrate NZ MPC-70, dry whey protein concentrate WPC34, and dry whey were mixed with water. Transglutaminase (12 g) (Ajinomoto Inc., Japan) containing about 1200 units of activity (where 1 unit is defined as the amount of enzyme that catalyzes the formation 1 micromole hydroxamate per minute under the assay conditions (Folk, J. E., et al., J. Biol. Chem. 240:2951 (1965))) dissolved in a small amount of water was added and incubated at 77° F. for 60 min. The resulting mixture was heated to 176° F. and held for 10 min. The heating was discontinued, and melted butter, a mixture of salt (sodium chloride), acid, and fine flake emulsifier salts (monosodium phosphate and disodium phosphate) were added, mixed for 10 min, and homogenized for 2 min further. In a separate vessel, the same cheese blend as used for the control was melted and blended with preblended colorants. The homogenized dairy liquid mixture, including the emulsifiers, was added to the well-melted cheese blend at about 160° F. and mixed for about 3 to 5 min. The mixture was heated at 176° F. for 1 min, and was passed through a vacuum flash tank to eliminate air bubbles. The resulting process cheese product was packaged and stored cold.

TABLE 1

Ingredients of process cheese compositions

| Component | Control (%) | Inventive Sample (%) |
|---|---|---|
| Cheese blend | 46.00 | 42.64 |
| Colorants | 0.03 | 0.03 |
| Anhydrous butter | 6.31 | 7.27 |

TABLE 1-continued

Ingredients of process cheese compositions

| Component | Control (%) | Inventive Sample (%) |
|---|---|---|
| Water | 28.31 | 27.82 |
| Salt | 0.93 | 0.93 |
| Emulsifiers (MSP, DSP) | 2.77 | 2.77 |
| WPC 34 and NZ MPC-70 | 5.63 | 5.63 |
| Dry whey | 9.92 | 12.78 |
| Sorbic acid | 0.10 | 0.10 |
| Transglutaminase | 0.000 | 0.028 |
| Total | 100.00 | 100.00 |

The preparations identified in Table 1 were examined for important physical properties. The melting area was measured by heating a cheese sample 4.3 cm in diameter, weighing 12.7±0.1 g, in an oven set at 85° C. for 11 min. The area that had melted was scanned and evaluated. The melting temperature was determined by using a Mettler FP 83HT dropping point cell (Mettler Toledo Ltd., Hightstown, N.J.). The process cheese samples were incubated at room temperature for 24 h before the assay. The temperature in the incubating chamber was increased from 35° C. at the rate of 2° C. per min until the cheese sample melted. Penetration was measured using a penetrometer (Precision Scientific, Bellwood, Ill.) at room temperature. The process cheese samples were incubated at room temperature for 24 h before the assay. The results are presented in Table 2.

TABLE 2

Properties of process cheese products.

| Property | Control | Inventive Sample |
|---|---|---|
| Melting area (mm$^2$) | 4206 | 5104 |
| Melting temperature (° C.) | 51.6 | 51.1 |
| Penetration (mm) | 13.1 | 13.3 |
| Lactose crystals present after 3 mos. refrigerated | None | None |

This experiment demonstrates the effects of incorporating increased lactose and whey protein into process cheese using the method of the invention. The inventive sample contained significantly more lactose and somewhat less water than does the control. It had slightly better melting behavior than did the control, and no lactose crystals were detected after three months storage at refrigerated temperature, even though the lactose in the moisture phase is supersaturated under these conditions (its concentration being about 18–19 percent). (This level of lactose in a conventional process cheese would be expected to form lactose crystals under these storage conditions.) These results suggest that 1) protein conjugates produced by transglutaminase crosslinking can be substituted in processed cheese for other cheese (in which the caseins are intact and thereby contribute to the body texture of the final product); 2) the presence of protein polymers crosslinked by transglutaminase efficiently retards the formation of lactose nuclei; and 3) the formation of transglutaminase crosslinked protein polymers in process cheese slightly improves the melting behavior of the final product. The present results on transglutaminase crosslinked protein conjugates indicate that they are more hydrophilic than the intact, or noncrosslinked, protein. The changed hydrophilicity may explain the improvement of melting properties of the processed cheese product. In addition it is estimated that the ingredients in the inventive formulation in Table 1 are about 2% less costly than those in the control formulation.

Example 2

Treatment of Dairy Liquid with Heat, Then with Transqlutaminase Prior to Addition to Melted Cheese An experimental composition incorporating the features of the invention was prepared and then compared with a control composition representative of process cheeses currently being marketed. Their respective compositions are presented in Table 3. The control sample was prepared as described above for Example 1 using another conventional cheese blend.

In order to prepare the inventive sample, milk protein concentrate NZ MPC-70, dry whey protein concentrate WPC34, and dry whey were mixed with water. This mixture was heated to 153° F. and held for about 5 min. The mixture was then allowed to cool to 123° F. Transglutaminase (15 g) (Ajinomoto Inc., Japan) containing about 1500 units of activity dissolved in a small amount of water was added and incubated at 123° F. for 30 min. Melted butter, a mixture of salts (sodium chloride), acid, and fine flake emulsifier salts (monosodium phosphate and disodium phosphate) were added, mixed for 10 min, and homogenized for 2 min further. In a separate vessel the same cheese blend as that used to prepare the process cheese of the control was melted and blended with the pre-blended colorants. The homogenized dairy liquid mixture including the emulsifiers was added to the well-melted cheese blend at about 160° F. and mixed for about 3 to 5 min. The mixture was heated at 176° F. for 1 min, and was passed through a vacuum flash tank to eliminate air bubbles. The resulting process cheese product was packaged and stored cold.

TABLE 3

Ingredients of process cheese compositions

| Component | Control (%) | Inventive Sample (%) |
| --- | --- | --- |
| Cheese blend | 46.00 | 42.13 |
| Colorants | 0.03 | 0.03 |
| Anhydrous butter | 6.31 | 6.72 |
| Water | 28.31 | 28.86 |
| Salt | 0.93 | 0.93 |
| Emulsifiers (MSP, DSP) | 2.77 | 2.77 |
| WPC 34 and NZ MPC-70 | 5.63 | 5.63 |
| Dry whey | 9.92 | 12.78 |
| Sorbic acid | 0.10 | 0.10 |
| Transglutaminase | 0.000 | 0.047 |
| Total | 100.00 | 100.00 |

The preparations identified in Table 3 were examined for important physical and organoleptic properties. The results for both preparations are presented in Table 4.

TABLE 4

Properties of process cheese products.

| Property | Control | Inventive Sample |
| --- | --- | --- |
| Melting area (mm$^2$) | 3607 | 4554 |
| Melting temperature (° C.) | 53.3 | 46.1 |
| Penetration (mm) | 12.5 | 15.8 |

TABLE 4-continued

Properties of process cheese products.

| Property | Control | Inventive Sample |
| --- | --- | --- |
| Lactose crystals present after 3 mos. refrigerated | None | None |

In this experiment, more water, more lactose, and slightly more whey protein are introduced into the inventive formulation than into the control formulation. In addition, the dairy liquid is brought to 153° F. then cooled prior to adding transglutaminase, and more transglutaminase was used to treat the inventive composition of this example than was used in Example 1. It is thought that the preliminary heat treatment partially denatured the proteins in the inventive formulation prior to the addition of transglutaminase. For these reasons, the extent of crosslinking of proteins by the enzyme could be greater than in Example 1, in which the preliminary heating step was omitted. In addition the crosslinked dairy liquid was not subjected to a prolonged heat treatment to inactivate the transglutaminase, further in contrast to the sample of Example 1.

The results of this experiment (Table 4) indicate that the presumed increased extent of crosslinking, the presence of residual transglutaminase activity, and the higher water content in the inventive sample significantly affect the behavior of the final product. Specifically, the process cheese that resulted had a softer texture (as shown by a penetration value of 15.8 mm compared to 12.5 mm for the control), a larger melting area (4554 mm$^2$ compared to 3607 mm$^2$ for the control), and a lower melting temperature than did the control (46.1° C. compared to 53.3° C). No lactose crystals were detected after three months storage at refrigerated temperature even though the lactose in the moisture phase is supersaturated under these conditions. (This level of lactose in a conventional process cheese would be expected to form lactose crystals under these storage conditions.) These results suggest that 1) the formation of crosslinked protein polymers in process cheese, using transglutaminase, can significantly influence the melting behavior and textural properties of the final product; and 2) the presence of protein polymers crosslinked by transglutaminase efficiently retards the formation of lactose nuclei. Furthermore, it is estimated that the ingredients in the inventive formulation of Table 3 are about 5% less costly than those constituting the control formulation.

Conventional production experience in cheese technology over several decades indicates that concentrations of lactose in the moisture phase of process cheeses greater than about 17% eventually leads to crystallization of the lactose after storage under refrigeration. Therefore, as a matter of practice the concentration of lactose has been limited to less than 17% in the moisture phase. For this reason, the ability in the present invention to preserve lactose at concentrations higher than this limit, corresponding to supersaturation, without crystallization of the lactose, by treating the proteins with transglutaminase, is unexpected in the field of process cheese manufacture, and surprising to workers in the cheese making arts.

We claim:

1. A process cheese product comprising a cheese and dairy liquid wherein the dairy liquid contains casein, whey protein, and lactose, wherein at least a portion of the casein or whey protein in the dairy liquid has been crosslinked via γ-carboxyl-ε-amino crosslinks with transglutaminase prior to being combined with the cheese, wherein the lactose in the process cheese product is contained as a non-crystalline material in a moisture phase in the process cheese product and remains dissolved upon storage at refrigerated temperature, and wherein the process cheese product is provided by a process that comprises the sequential steps of (i) preparing a dairy liquid comprising casein, whey protein, and lactose;

(ii) contacting the dairy liquid with a transglutaminase for a time, and under conditions, sufficient to crosslink at least a portion of the casein and/or whey protein to provide a crosslinked dairy liquid;

(iii) combining the crosslinked dairy liquid with one or more compositions wherein the compositions taken together include a fat, an emulsifier, a salt, and a preservative, and homogenizing the combination;

(iv) adding the homogenized combination to a melted cheese to form a process cheese; and (v) heating the process cheese to a temperature of 170° F. to 200° F. for about 1 min to 10 min to form the process cheese product.

2. The process cheese product as described in claim 1, wherein the transglutaminase is a transglutaminase isolated from the group consisting of a microbial source, a fungus, a mold, a plant, a fish, and a mammal.

3. The process cheese product as described in claim 1, wherein the transglutaminase is isolated from a microbial source.

4. The process cheese product as described in claim 1, wherein the transglutaminase is isolated from the genus Streptoverticillium.

5. The process cheese product as described in claim 1, wherein the process further comprises heating the dairy liquid at a temperature between about 130° F. and about 200° F. for a time between about 2 minutes and about 100 minutes after step (i) and before step (ii).

6. The process cheese product as described in claim 1, wherein the dairy liquid is contacted with transglutaminase at a temperature from about 50° F. to about 150° F. for a time between about 10 minutes and about 300 minutes.

7. The process cheese product as described in claim 6, wherein the temperature is from about 75° F. to about 125° F. and the time is between about 30 minutes and about 60 minutes.

8. The process cheese product as described in claim 1, wherein the process further comprises heating the crosslinked dairy liquid at a temperature and for a time sufficient to inactivate the transglutaminase after step (ii) and before step (iii).

9. The process cheese product of claim 1, wherein lactose in the moisture phase of the process cheese product is at a supersaturated level.

10. The process cheese product of claim 1, wherein the process does not include a heat treatment step after contacting the dairy liquid with the transglutaminase to provide the crosslinked dairy liquid.

11. A process for making a process cheese product comprising the sequential steps of (i) preparing a dairy liquid comprising casein, whey protein, and lactose;

(ii) contacting the dairy liquid with a transglutaminase for a time, and under conditions, sufficient to crosslink at least a portion of the casein or whey protein to provide a crosslinked dairy liquid;

(iii) combining the crosslinked dairy liquid with one or more compositions wherein the compositions taken together include a fat, an emulsifier, a salt, and a preservative, and homogenizing the combination;

(iv) adding the homogenized combination to a melted cheese to form the process cheese; and (v) heating the process cheese to a temperature of 170° F. to 200° F. for 1 min to 10 min;

wherein at least a portion of the casein or whey protein is crosslinked via $\gamma$-carboxyl-$\epsilon$-amino crosslinks, and wherein the lactose in the process cheese remains dissolved in the aqueous phase upon storage at refrigerated temperature.

12. The process as described in claim 11, wherein the transglutaminase is selected from the group of transglutaminases isolated from a bacterial source, a fungus, a mold, a plant, a fish, and a mammal.

13. The process as described in claim 11, wherein the transglutaminase is isolated from a microbial source.

14. The process as described in claim 11, wherein the transglutaminase is isolated from the genus Streptoverticillium.

15. The process as described in claim 11, wherein the process further comprises heating the dairy liquid at a temperature between about 130° F. and about 200° F. for a time between about 2 minutes and about 100 minutes after step (i) and before step (ii).

16. The process as described in claim 12, wherein the process further comprises heating the dairy liquid at a temperature between about 130° F. and about 200° F. for a time between about 2 minutes and about 100 minutes after step (i) and before step (ii).

17. The process as described in claim 11, wherein the dairy liquid is contacted with transglutaminase at a temperature from about 50° F. to about 150° F. for a time between about 10 minutes and about 300 minutes.

18. The process as described in claim 17, wherein the temperature is from about 75° F. to about 125° F. and the time is between about 30 minutes and about 60 minutes.

19. The process as described in claim 11, wherein the process further comprises heating the crosslinked dairy liquid at a temperature and for a time sufficient to inactivate the transglutaminase after step (ii) and before step (iii).

20. The process of claim 11, wherein lactose in the aqueous phase of the process cheese is at a supersaturated level.

21. The process of claim 11, wherein the process does not include a heat treatment step after contacting the dairy liquid with the transglutaminase to provide the crosslinked dairy liquid.

* * * * *